United States Patent [19]

Nehrich, Jr. et al.

[11] 3,934,149

[45] Jan. 20, 1976

[54] METHOD OF IDENTIFYING ENEMY FORCES

[76] Inventors: Richard B. Nehrich, Jr., 4019 Marlesta Drive, San Diego, Calif. 92111; David K. Forbes, 2216 Crownhill Road, San Diego, Calif. 92109

[22] Filed: Aug. 19, 1974

[21] Appl. No.: 498,354

Related U.S. Application Data

[63] Continuation-in-part of Ser. No. 726,615, May 3, 1968, abandoned.

[52] U.S. Cl. .................................. 250/459; 250/461
[51] Int. Cl.² ........................................ G01N 21/38
[58] Field of Search ............ 250/302, 303, 361–369, 250/458–467

[56] References Cited
UNITED STATES PATENTS
3,358,602  12/1967  Chope ............................ 250/493 X

OTHER PUBLICATIONS

Catalog No. 127, Sirchie Finger Print Laboratories, July 11, 1951, p. 45, HV8073 S4 1951.
Marshall, "That New Black Magic", *Colliers*, Sept. 30, 1944, p. 66, p. 74.

*Primary Examiner*—Davis L. Willis
*Attorney, Agent, or Firm*—R. S. Sciascia; G. J. Rubens

[57]     ABSTRACT

Infiltrators into protected zones are identified by depositing a tacky narrow band fluorescent material, on a perimeter portion of the zone, by illuminating infiltrators of the perimeter with a beam of ultra-violet light and by spectroscopically analyzing a telescopic-received image of the illumination. Most suitably, the fluorescent material is a europium chelate composition, such as europium trifluoracetonate dissolved in acetonitrile and added to an uncatalyzed resin.

1 Claim, 2 Drawing Figures

U.S. Patent   Jan. 20, 1976   3,934,149
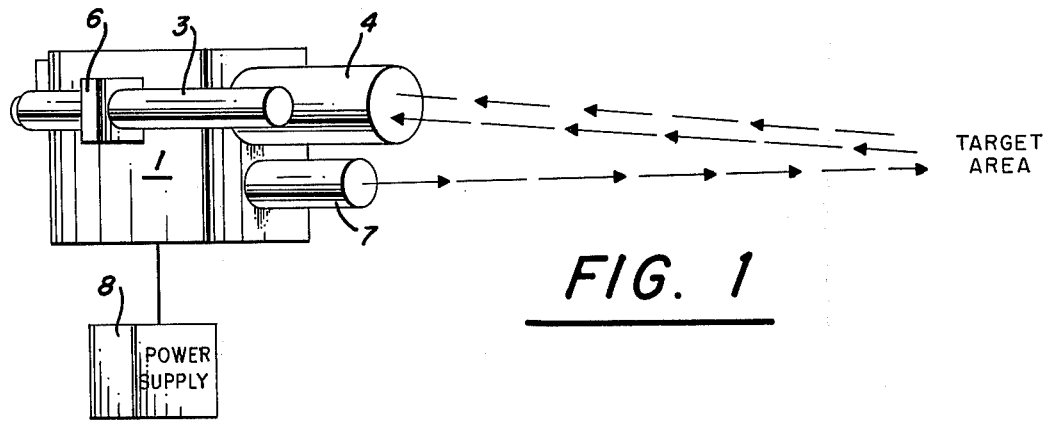
FIG. 1
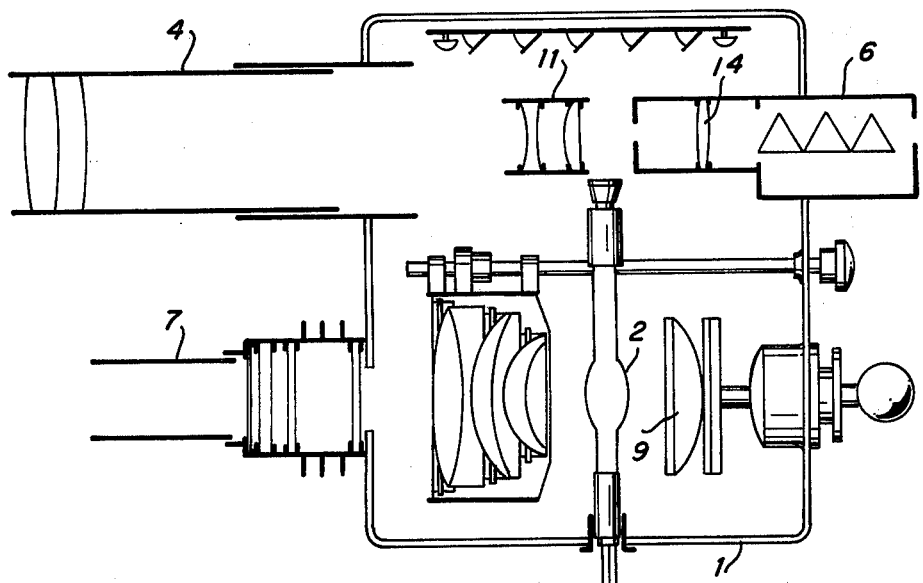
FIG. 2
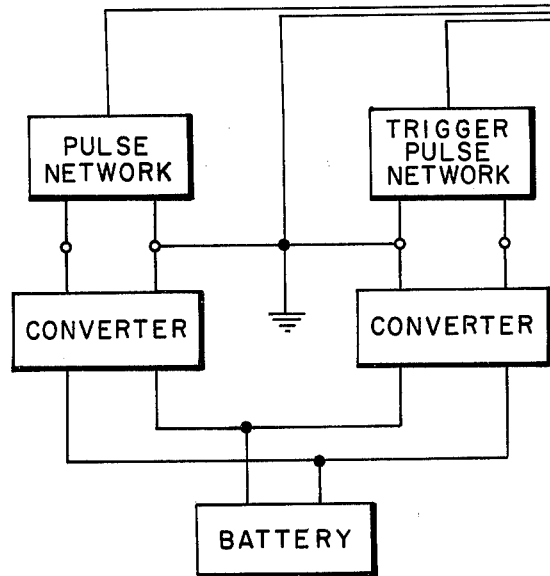
INVENTORS
RICHARD B. NEHRICH, JR.
DAVID K. FORBES
BY
ATTORNEYS

METHOD OF IDENTIFYING ENEMY FORCES

STATEMENT OF GOVERNMENT INTEREST

The invention described herein may be manufactured and used by or for the Government of the United States of America for governmental purposes without the payment of any royalties thereon or therefor.

CROSS-REFERENCES TO RELATED APPLICATIONS

This application is a continuation-in-part of application Ser. No. 726,615 filed May 3, 1968 now abandoned.

BACKGROUND OF THE INVENTION

In combat areas, such as Vietnam, it has proven extremely difficult to distinguish between friendly and unfriendly native forces. Individual screening and interrogation is not always possible or feasible and, frequently, it simply compounds the confusion. Substantial efforts have been devoted toward providing a more reliable means of identification, the instant proposal being to deposit fluorescent materials on the perimeter of a particular zone. Infiltrators pick up the fluorescent material permitting identification to be made.

Such a concept is entirely feasible, but there have been difficulties both in providing suitable marker materials and in developing adequate means for producing and viewing the fluorescence. While there are a number of devices capable of both illuminating and viewing fluorescence at close range, such a procedure requires personal and individual contact with the suspect and therefore does not permit a broad scanning of an area such as would enable a suspect to be picked out of a relatively large group. One complication arising particularly during daylight hours is that the fluorescence is relatively dim and difficult to detect particularly when sunlight or other light sources produce interfering backgrounds.

Also, from a practical point of view, apparatus suitable for such uses should be easily portable and also relatively inexpensive if it is to be used extensively in the field. Expensive, heavy equipment which conceivably might generate sufficient power to accomplish the present purposes are not acceptable.

OBJECTS OF THE INVENTION

One of the objects of the present invention is to provide a method of identifying the infiltrators, the method permitting identifications to be made at substantial distances from the suspect and also permitting the use of inexpensive, lightweight, portable apparatus.

A further object is to provide an identification method in which the fluorescence to be detected is clearly distinguishable from interfering background fluorescences.

Another object is to provide a marker material capable of use with the methods of the foregoing objects.

Other objects will become more apparent in the detailed description which is to follow.

BRIEF DESCRIPTION OF THE DRAWINGS

FIG. 1 illustrates the manner in which the present identification method is conducted, and FIG. 2 is a sectional view of apparatus suitable for accomplishing the present purposes.

DESCRIPTION OF THE PREFERRED EMBODIMENTS

It first is to be noted that the apparatus illustrated in FIGS. 1 and 2 also is disclosed and claimed in a copending patent application by the same inventors and entitled "Apparatus for Viewing a Distant Fluorescent Object", Ser. No. 726,617 issued as U.S. Pat. No. 3,836,782. This apparatus, as well as other comparable apparatus, can be used to perform the present identification method and also it can be employed to detect the fluorescence of the marker material which forms a part of the present invention.

A detailed understanding of the illustrated apparatus is not essential for present purposes. Briefly considered, it is mounted in a portable casing 1 preferably supported on a tripod or the like to permit training and elevation for scanning purposes. A short-arc ultra-violet light source 2 produces a beam of ultra-violet light to illuminate a target which, according to the present method, would be a suspect individual or possibly a boat or other piece of equipment which for purpose of this application may be referred to collectively as infiltrators. The fluorescent marker material which will be described later is detectable through a telescope 3 mounted on the side of casing 1. Also, the fluorescence can be both viewed and analyzed through another telescope 4 provided with an optical system capable of focusing the received image into a spectroscope 6.

In illuminating the target, light from source 2 is projected in a beam cylindrical portion 7 of the casing, the beam having an optical axis substantially parallel to the optical axes of the receiving telescopes. The light source is energized by a standard 24-volt battery 8 and, preferably, the source is pulsed through an appropriate pulse network coupled between the electrodes of the light source and the battery. Conservation of the battery power can be achieved by varying the source pulse rate to suit operating conditions, the variable pulse rate being achieved in any conventional manner such as the use of electronic circuitry including a silicon controlled rectifier. Since the range of the projected beam is a significant consideration, it is desirable to utilize all of the light generated by the source and certain components, such as a spherical mirror 9 disposed behind the source, can be employed to gather and concentrate the generated light. The optical systems employed in the apparatus are somewhat conventional in that they include a standard arrangement of lenses forming a light gathering and collimating unit 11 and certain ultra-violet transmitting filters carried in cylindrical portion 7. The optics of the telescopes also are conventional although it is important that a unit, such as unit 11, be employed to collimate and focus all of the received image onto an objective lens 14 of the spectroscope. A system, such as that employed in this apparatus, is capable of illuminating and viewing targets in a zone at distances upwards of 150 yards, which can be considered as being a remote area capable of telescopic viewing. In this regard, another significant factor determining maximum range is the brilliance or intensity of the fluorescence of the marker material.

One of the features of the present invention is the use of a particular composition as a marker material. Since the present method includes a spectroscopic analysis of the fluorescence of the material, one of the prime requisites is that any such material must be characterized by its narrow spectral-bandwidth to enable the concentrated energy to be detected by the eye and distinguished from the background fluorescence due to the sunlight. In addition, its fluorescence must be unusually intense and bright to enhance the range of the surveillance. Such criteria are fulfilled by employing compositions formulated with rare earth chelates of the lanthanide series such, for example, as the europium chelates. In particular, europium trifluoroacetone and europium benzoylacetonate prepared with acetonitrile provide an unusually narrow emission bandwidth of a bright red-orange hue that yields maximum contrast relative to background light. Such chelates are known in the prior art and their preparations described in a published article "Stimulated Emission in an Europium Chelate Solution at Room Temperature." Fluorescent materials in the range of 100 angstroms or less are classifiable as having a "narrow" bandwidth, and the above described fluorescent materials which have been found in tests to be particularly suitable fall within this definition.

Formulations incorporating these chelates should be related to the intended use of the marker material, it being noted that the material may be deposited on foliage of a zone perimeter, or, in some applications, on the water of rivers or other bodies of water. Compositions formulated for dispersion on foliage preferably utilize a clear, colorless, very sticky, uncatalyzed polyester resin such as Rezyl 315 or Pittsburg 500–48. The Rezyl resin is a proprietary product of American Cyanamid Company and the Pittsburg resin is a commercial product produced by Pittsburg Coke and Chemical Company. In preparing the marker composition, the selected resin is thinned with any commercially available thinner, such as xylol, toluene or xylene, to the desired physical condition best suited for application. Thus, if the resin is to be deposited by a spraying, it is thinned to such a point that spraying is permissible. Europium chelate then is dissolved in a small amount of acetonitrile in accordance with the teachings of the previously-mentioned publication and the acetonitrile solution added to the resin to provide 1–5% by weight of the chelate in the mixture.

A water-borne composition, preferably employs a polyurethane resin in place of the polyester resin, the polyurethane resin being clear, uncatalyzed, and physically capable of forming a tacky film on water. One resin suitable for the water-borne purposes is polyurethane Spenkle F–77–60X, a proprietary product of Spencer-Kellogg & Sons, Inc. Again, the europium chelate is dissolved in acetonitrile and added to the resin to provide about 1–3% chelate by weight. Other resins, of course, may be found suitable for either foliage or water-borne uses. Also, it may be found desirable to utilize fluorescent materials of different colors for different perimeter zones. An appropriate substitute for the europium chelate is a terbium chelate which provides a narrow emission bandwidth of a bright green color. Either of these chelates allow both visual detection and spectroscopic analysis and they both are particularly beneficial for sunlight surveillance in which contrast enhancement relative to background interference is important.

Another feature of the present invention is the method or manner in which this material is used to identify infiltrators or unfriendly forces penetrating a protected zone or encampment. As has been indicated, the method contemplates depositing the marker material on a perimeter portion of the zone which may either be foliage or water and the dispersion and deposition of the material preferably is accomplished by spraying techniques. The apparatus previously described with reference to FIGS. 1 and 2 is employed to scan suspected infiltrators of the perimeter with its beam of ultra-violet light and, of course, if the infiltrator has picked up any of the marker material, the illumination will produce the bright narrow band fluorescent emission. Scanning can be accomplished by employing telescope 3 which, particularly at night, should easily pick out the fluorescent emission. The emission then can be studied spectroscopically using spectroscope 6 of the apparatus. Alternatively, telescope 4 which provides the input for the spectroscope can be used for initial scanning purposes although it will be found that telescope 3, due to its broader field, may facilitate this phase of the detection. In any event, final analysis and resolution of the identification problem contemplates the use of the spectroscope image.

The advantages of the present marker material and the method in which it is used have been stated. One principal advantage is that the method permits the scanning operation to select suspects from an entire group. Consequently, it eliminates the need for individually interrogating each suspect although, of course, selected suspects would be questioned since conceivably the fluorescent material could have been picked up inadvertently. Also, the spectroscopic analysis permits the use of a relatively small size, low-powered field instrument which is sufficiently inexpensive and simple to justify extensive use. The particular marker material significantly enhances the present method since it expands its range due to the brilliance of its fluorescent emission. Further, the particular compositions provided by the present invention are physically capable of wide dispersion and, due to their colorless nature, are not susceptible of being detected by the infiltrators.

Obviously many modifications and variations of the present invention are possible in the light of the above teachings. It is therefore to be understood that within the scope of the appended claims the invention may be practiced otherwise than as specifically described.

What is claimed is:
1. A method of identifying infiltrators at a distance up to 150 yards in sunlight and nighttime conditions that have passed through a protected outdoor zone comprising the steps of:
depositing a tacky, high intensity, fluorescent material having a narrow spectral bandwidth in the range of 100 angstroms or less over a perimeter portion of the surface of said outdoor zone;
illuminating from a remote observation station infiltrators of said perimeter having contacted the fluorescent material with a beam of ultraviolet;
telescopically receiving at said station an image of said illuminated infiltrators;
spectroscopically analyzing at said station said telescopically received image of said illumination to observe the presence of said narrow bandwidth fluorescent material characterized by a sharp spike-like energy emission, enabling distinctive visual discrimination between the fluorescent light from the marked infiltrator and the fluorescent light of any reflected sunlight from the zone.

* * * * *